(12) United States Patent
Breeden et al.

(10) Patent No.: US 11,591,283 B2
(45) Date of Patent: Feb. 28, 2023

(54) PROCESS FOR THE PRODUCTION OF DIALKYL TEREPHTHALATE

(71) Applicant: Conopco, Inc., Englewood Cliffs, NJ (US)

(72) Inventors: Simon William Breeden, York (GB);
James Hanley Clark, York (GB);
Thomas James Farmer, York (GB);
Duncan James MacQuarrie, York (GB); Con Robert McElroy, York (GB); Joseph Kolawole Ogunjobi, Akure (NG); David William Thornthwaite, Little Neston (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/981,964

(22) PCT Filed: Mar. 28, 2019

(86) PCT No.: PCT/EP2019/057916
§ 371 (c)(1),
(2) Date: Sep. 17, 2020

(87) PCT Pub. No.: WO2019/201569
PCT Pub. Date: Oct. 24, 2019

(65) Prior Publication Data
US 2021/0122698 A1 Apr. 29, 2021

(30) Foreign Application Priority Data
Apr. 18, 2018 (EP) .................................. 18168062

(51) Int. Cl.
| | | |
|---|---|---|
| *C07C 67/347* | (2006.01) | |
| *B01J 21/16* | (2006.01) | |
| *B01J 37/30* | (2006.01) | |
| *C07C 69/82* | (2006.01) | |

(52) U.S. Cl.
CPC .............. *C07C 67/347* (2013.01); *B01J 21/16* (2013.01); *B01J 37/30* (2013.01); *C07C 69/82* (2013.01)

(58) Field of Classification Search
CPC ........ C07C 67/347; C07C 69/82; B01J 21/16; B01J 37/30; F16L 21/03; F16L 21/08; F16L 33/20; F16L 47/08; F16L 47/12; F16L 5/10; F28F 9/007; H01M 10/613; H01M 10/625; H01M 10/647; H01M 10/6552; H01M 10/6556; H01M 10/6557; H01M 10/6567; H01M 10/6568; H01M 2220/20; H01M 50/249; H01M 50/691; Y02E 60/10
See application file for complete search history.

(56) References Cited

U.S. PATENT DOCUMENTS

| | | | | |
|---|---|---|---|---|
| 4,018,742 A | * | 4/1977 | Suzuki | C08G 73/16 528/291 |
| 4,780,552 A | | 10/1988 | Wambach et al. | |
| 9,321,714 B1 | | 4/2016 | Brandvold et al. | |
| 2010/0331568 A1 | | 12/2010 | Brandvold | |
| 2011/0087000 A1 | | 4/2011 | Peters et al. | |
| 2012/0107892 A1 | * | 5/2012 | Agbogbo | C12P 7/065 435/162 |
| 2014/0364631 A1 | * | 12/2014 | Davis | C07C 67/343 549/463 |

FOREIGN PATENT DOCUMENTS

| | | | |
|---|---|---|---|
| EP | 2481733 | * | 8/2012 |
| EP | 3257886 | * | 12/2017 |
| WO | WO2009064515 | | 5/2009 |
| WO | WO2009120457 | | 10/2009 |
| WO | WO2010099201 | | 9/2010 |

OTHER PUBLICATIONS

Negendrappa et al. (Organic Synthesis using Clay Catalysts, Clays for Green Chemistry, Resonance, pp. 64-77, published Jan. 2002) (Year: 2002).*
Kawabata et al. (Monomeric Metal Aqua Complexes in the Interlayer Space of Montmorillionites as Strong Lewis Acid Catalysts for Heterogeneous Carbon-Carbon Bond-Forming Reactions, Chemistry A European Journal, 11, pp. 288-297, published 2005) (Year: 2005).*
Search Report in EP18168062; dated Oct. 19, 2018; European Patent Office (EPO).
Search Report and Written Opinion in PCTEP2019057916; dated Jun. 27, 2019.
Lyons et al.; Synthesis of p-Xylene from Ethylene; Journal of the American Chemical Society; Aug. 30, 2012; pp. 15708-15711; vol. 134; ACS Publications; United States of America.
Roger A. Sheldon; Green and sustainable manufacture of chemicals from biomass: state of the art; Green Chemistry; Nov. 26, 2013; pp. 950-963; vol. 16; Royal Society of Chemistry.
Tachibana et al.; Synthesis and Verification of Biobased Terephthalic Acid from Furfural; Scientific Reports; Feb. 4, 2015; pp. 1-5; vol. 5: 8249.

* cited by examiner

Primary Examiner — Yevgeny Valenrod
Assistant Examiner — Blaine G Doletski
(74) Attorney, Agent, or Firm — Foley & Lardner LLP

(57) ABSTRACT

A process for preparing dialkyl terephalate comprising the following steps:—i) providing furan-2,5-dicarboxylate; ii) esterifying the furan-2,5-dicarboxylate with alcohol to form furan-2,5-carboxylic acid dialkyl ester; iii) reacting the furan-2,5-carboxylic acid dialkyl ester with ethylene under Diels Alder conditions, elevated temperature and pressure and in the presence of a catalyst such that dialkyl terephthalate is produced; wherein the Diels-Alder reaction is free from solvent; wherein the catalyst comprises a clay comprising metal ions and having Lewis acidity.

22 Claims, No Drawings

PROCESS FOR THE PRODUCTION OF DIALKYL TEREPHTHALATE

CROSS-REFERENCE TO RELATED APPLICATIONS

The present application is a U.S. National Phase Application under 35 U.S.C. § 371 of International Application No. PCT/EP2019/057916, filed on Mar. 28, 2019, which claims priority to European patent application No. 18168062.0 filed on Apr. 18, 2018, the contents of which are incorporated herein in their entireties.

FIELD OF THE INVENTION

The invention relates to a process for preparing bio-based terephthalic acid, specifically from a furan-2,5-dicarboxylate that utilises a novel catalyst. Terephthalic acid has major application in the production of materials such as polyethylene terephthalate (PET), which in turn is a key component of many plastic containers.

BACKGROUND OF THE INVENTION

Terephthalic acid (TA) and other aromatic carboxylic acids are widely used in the manufacture of polyesters, commonly by reaction with ethylene glycol, higher alkylene glycols or combinations thereof, for conversion to fibre, film, containers, bottles, packaging materials and moulded articles. An important polyester of this type is polyethylene terephthalate (PET), derived from the esterification of terephthalic acid, or transesterification of dialkyl terephthalate, with ethylene glycol. PET is ideal for use in packaging applications owing to its durability, high resistance to oxygen and water, low weight to filling volume, low permeability to gas and non-toxicity to humans. Current global PET production exceeds 50 million tonnes per annum.

A particularly advantageous benefit in the use of PET is its ease of recycling, typically either via melting and reforming or via depolymerisation (hydrolysis, alcoholysis or glycolysis) to reform the constituent monomer units. Recycling of PET does not result in the excessive loss of mechanical properties, so it can be reused many times, thus reducing gas emissions and saving energy.

It follows that a sustainable process for the production of PET from biomass is also desirable. The fluctuating cost of petroleum and the reduction in global crude oil reserve impacts current PET production processes, making them increasingly expensive and unsustainable. Also desirable are new improved processes for the production of the constituent monomers used in the production of PET. A successful example is the production of ethylene glycol (EG), historically synthesised solely from petroleum sources, which accounts for 30% w/w of PET. EG can now be obtained from bio-derived ethylene or from platform molecules such as sorbitol and xylitol. The production of TA by oxidation of p-xylene, however, represents the second largest global consumption of acetic acid; a process which is very environmentally damaging. P-xylene itself is a fossil-derived chemical and accounts for the remaining 70% w/w of PET, but there is no simple bio-replacement for this molecule.

A number of routes have been explored in attempts to obtain bio-derived terephthalic acid.

The first route is via 5-hydroxymethyl furfural (HMF) which is sourced from glucose or cellulose. For example, US-A-2010331568 describes a catalytic process for the conversion of DMF to para-xylene, where the DMF starting material may be synthesized from carbohydrates (e.g., glucose or fructose).

Another route, disclosed in US-A-2011087000 utilises fermentation of sugar to isobutanol followed by dehydration to isobutene, which upon dimerisation, dehydrocyclisation and oxidation of product gives a bio-derived TA.

A third route converts sugar beets to a mixture of intermediates which are further processed to give para-xylene as one of the products; see for example, Sheldon, R. A. Green and Sustainable Manufacture of Chemicals from Biomass: State of the Art; *Green Chemistry* 16, 950-963 (2014). This route also forms the basis for production bio-based PET, described in WO-A-2009/120457.

A further route, the "absolute ethane route" utilises ethene as the sole starting material to obtain para-xylene (Route D); Lyons, T. W., Guironnet, D., Findlater, M. & Brookhart, M.; Synthesis of p-Xylene from Ethylene. *Journal of the American Chemical Society* 134, 15708-15711 (2012). The synthesis proceeds via trimerisation of ethene to hexene, conversion to hexadiene over an iridium complex catalyst, Diels-Alder addition of ethene to hexdiene and then catalytic dehydrogenation of the product 3,6-dimethyl cyclohexene.

Finally, the "absolute furfural route" proceeds via oxidation of furfural to fumaric and maleic acids, which are subsequently dehydrated to maleic anhydride. Diels-Alder addition of furan (obtainable from decarbonylation of furfural) (disclosed in U.S. Pat. No. 4,780,552) to maleic anhydride gives an exo-DA adduct which is subsequently converted to anhydride and phthalate salt and finally to TA. Analysis of the obtained TA with accelerator mass spectroscopy showed it had a 100% bio-based carbon content (Tachibana, Y., Kimura, S. & Kasuya, K.-i. Synthesis and Verification of Biobased Terephthalic Acid from Furfural. *Scientific Reports* 5, 8249, doi:10.1038/srep08249; 2015).

WO-A-2010/099201 (Gevo Inc) discloses methods for producing isobutene, isoprene, and butadiene from mixtures of C4 and/or C5 olefins by dehydrogenation. The C4 and/or C5 olefins can be obtained by dehydration of C4 and C5 alcohols, for example, renewable C4 and C5 alcohols prepared from biomass by thermochemical or fermentation processes. Isoprene or butadiene are then polymerized to form polymers such as polyisoprene, polybutadiene, synthetic rubbers such as butyl rubber, etc. in addition, butadiene can be converted to monomers such as methyl methacrylate, adipic acid, adiponitrile, 1,4-butadiene, etc. which can then be polymerized to form nylons, polyesters, polymethylmethacrylate etc.

WO-A-2009/120457 (The Coca-Cola Company) discloses a bio-based polyethylene terephthalate polymer comprising from 25 to 75 wt % of a terephthalate, which is selected from terephthalic acid, dimethyl terephthalate, isophthalic acid, and a combination thereof; and from 20 to 50 wt % of a diol selected from ethylene glycol, cyclohexane dimethanol, and a combination thereof; wherein at least 1 wt % of the terephthalate and/or the diol is derived from bio-based material. Also disclosed is a method of producing a bio-based polyethylene terephthalate polymer comprising a) obtaining a diol comprising ethylene glycol; b) obtaining a terephthalate comprising terephthalic acid, wherein the diol and/or the terephthalate is derived from bio-based material; and c) reacting the diol and the terephthalate to form a bio based polyethylene terephthalate polymer, which comprises from 25 to 75 wt % of the terephthalate and from 20 to 50 wt % of the diol.

WO-A-2009/064515 (BP Corporation N. Am. Inc) discloses a process for the production of terephthalic acid comprising a) reacting a 2,5-furandicarboxylate with ethylene in the presence of a solvent to produce a bicyclic ether; and b) dehydrating the bicyclic ether. Also disclosed is a terephthalic acid composition having a purity sufficient for direct conversion by reaction with a least one glycol to polyester, suitable for the manufacture of fibre and film without additional purification comprising less than about 25 ppm of 2,5-furan-dicarboxylic acid as an impurity.

U.S. Pat. No. 9,321,714 (UOP LLC) discloses a process of making terephthalic acid or a derivative of terephthalic acid comprising: reacting a diester derivative of 2,5-dimethylfuran with a dienophile containing an unsaturated 2-carbon unit, in the presence of a catalyst to form a para-xylene derivative and optionally reacting the para-xylene derivative to terephthalic acid. The catalyst comprises a metal oxide having Bronsted acidity and further comprises an electron rich metal promoter. Suitable catalysts include solid acid catalysts, metal oxides, ionic liquids, and zeolites. A preferred catalyst is tungstated zirconia.

Despite the prior art, the problem remains that the starting biomass has first to be reduced with oxygen atoms partially or completely removed, and thereafter oxidised to form TA. This has considerable impact on the atom economy of the processes. Additionally, the oxidation step employs the same harsh and destructive reaction conditions currently employed in typical TA synthesis. Atom economy is the measurement of how many atoms of reactants end up in the final product and how many end up in by-products or waste, and is a useful indicator of the environmental impact of a given reaction.

We have now found that a route involving the synthesis of dialkyl terepthalate (preferably diethyl terephthalate (DET) as a potential precursor for bio-based PET) via Diels-Alder addition of 2,5-furandicarboxylic acid to ethene using a heterogeneous, clay-based catalyst results in a yield and selectivity higher than any other reported route. The route is solventless, and involves fewer steps than the prior art.

SUMMARY OF THE INVENTION

A first aspect of the present invention provides a process for preparing dialkylterephalate comprising the following steps:
 i) providing furan-2,5-dicarboxylate;
 ii) esterifying with alcohol to form furan-2,5-carboxylic acid dialkyl ester;
 iii) reacting the furan-2,5-carboxylic acid dialkyl ester with ethylene under Diels Alder conditions, elevated temperature and pressure and in the presence of a catalyst such that dialkyl terephthalate is produced;
 wherein the Diels-Alder reaction is free from solvent;
 wherein the catalyst comprises a clay comprising metal ions and having Lewis acidity.

Preferably, the process further comprises the step of converting the dialkyl terephthalate into a further product, preferably selected from the group consisting of terephthalate polyesters (preferably polyethylene terephthalate), poly(butyleneterphalate-co-butyleneadipate (PBAT), and terephthalate plasticizers (which are terephthalate diesters where the alkyl groups are longer carbon chains selected from straight and branched). Preferably, diethyl terephthalate is converted into polyethylene terephthalate.

Preferably, the process is a batch process. Sublimation is a particular problem in a batch process and not in a flow system.

DETAILED DESCRIPTION OF THE INVENTION

The term "bio-based," as used in the context of the presence invention, preferably indicates the inclusion of some component that derives from at least one bio-based material. For example, a "bio-based PET polymer" would be a PET polymer that comprises at least one component that partially or totally derives from at least one bio-based material.

The furan-2,5-dicarboxylate

The furan-2,5-dicarboxylate for use in the process of the invention is preferably waste derived, for example, from carbohydrate, cellulose or lignocellulosic waste.

The Alcohol and the Esterification Reaction

The furan-2,5-dicarboxylate is esterified using an alcohol, preferably a bioalcohol to form furan-2,5-carboxylic acid alkyl ester.

The furan-2,5-carboxylic acid dialkyl ester is preferably furan-2,5-carboxylic acid diethyl ester.

A bioalcohol is an alcohol that is produced through contemporary biological processes, such as agriculture and anaerobic digestion, rather than from fossil fuels, such as coal and petroleum. For example, bioethanol is made by fermentation, mostly from carbohydrates produced in sugar or starch crops such as corn, sugarcane, or sweet sorghum. Cellulosic biomass, derived from non-food sources, such as trees and grasses, is also being developed as a feedstock for bioethanol production.

Preferably the alcohol has 1 to 9 carbon atoms, more preferably from 1 to 4 carbon atoms, most preferably from 1 to 3 carbon atoms.

The alcohol may be aliphatic, benzyl or phenolic in nature, preferably aliphatic.

The alcohol may be straight chain or branched, preferably straight.

More preferably the alcohol is straight chain aliphatic of 1 to 4 carbon atoms, preferably 1 to 3 carbon atoms.

Preferably the alcohol has a boiling point of up to 200° C., more preferably less than 120° C., most preferably up to 100° C.

Preferably the alcohol is selected from the group consisting of bio-methanol, bio-ethanol, bio-propanol, and mixtures thereof. The most preferred alcohol is bio-ethanol.

The esterification reaction is preferably carried out in the presence of an acid catalyst, and excess alcohol. The acid catalyst is preferably selected from sulphuric acid, toluene sulphonic acid and sulphonic acid resin polymer, preferably sulphuric acid. The sulphonic acid resin polymer is environmentally advantageous because it is solid, recoverable and reusable.

Diels-Alder Addition of furan-2,5-carboxylic acid dialkyl ester to ethylene

The product of step ii) (furan-2,5-carboxylic acid dialkyl ester) is reacted with ethylene to form dialkyl terephthalate under Diels Alder conditions, in the presence of a catalyst such that dialkyl terephthalate is produced.

Where the product of step ii) is furan-2,5-carboxylic acid dethyl ester, it is reacted with ethylene to form diethylalkyl terephthalate under Diels Alder conditions, in the presence of a catalyst such that diethyl terephthalate is produced.

The reaction is pressurized, for example using a high-pressure reactor. The filling pressure is preferably from 20 to 300 bar, more preferably from 30 to 250 bar, even more preferably from 30 to 200 bar, most preferably from 40 to 100 bar.

In addition, a temperature of from 50 to 400° C., more preferably from 100 to 300° C., most preferably from 120 to 280° C. is utilized. Both temperature and pressure should be selected according to the exact nature of the catalyst, as different catalysts work at different temperatures and pressures.

An intermediate is formed during the Diels-Alder reaction. The first step of the Diels-Alder reaction forms a bi-cyclic oxo-adduct, which auto-aromatises via dehydration under the high temperature acidic conditions of the reaction, thus forming the desired dialkyl terephthalate, which is preferably diethyl terephthalate.

The Diels-Alder reaction may suitably be carried out below the critical point of ethene, for example, at a pressure of from 20 to 40 bar. If necessary, dissolution of the furan-2,5-carboxylic acid dialkyl ester may be required to prevent sublimation.

The Diels-Alder reaction of the process of the invention is carried out in a solvent-free environment. The use of a solvent-free reaction resulted in high yields of diethyl terephthalate.

Attempts to use solvents, for example ethanol and water, were found to be unsuccessful with no formation of terephthalate or the oxo-adduct observed.

The Ethylene

The process of the invention utilises ethylene. The ethylene is preferably bioderived from biomass feedstock. Bioethylene is produced from bioethanol.

The Catalyst

The process of the invention utilises a heterogeneous catalyst that comprises a clay. Heterogeneous catalysts are advantageous because they are recoverable and reusable.

The clay may be a natural, synthetic or chemically modified clay. It is preferably a smectite clay. The term smectite clay as used herein includes clays in which aluminium oxide is present in a silicate lattice as well as clays in which magnesium oxide is present in a silicate lattice.

Specific examples of suitable smectite clays include those selected from the classes of the montmorillonites, hectorites, volchonskoites, nontronites, saponites, beidelites and sauconites. Preferably, the clay is a montmorillonite.

Preferred chemically modified clays are selected from cation-exchanged clays and pillared clays, preferably pillared clays. Cation-exchanged clays are clays in which cations, typically metal Lewis acid cations, have been introduced into the interlamellar spaces of the layered structure of the clay, typically by ion-exchange. Pillared clays are treated such that large metal polycations are introduced into the layered structure of the clay, forming a porous structure that, once calcined, is thermally stable. A commercially available example of an aluminium pillared clay is available from Sigma-Aldrich.

The clay catalyst exhibits inherent Lewis acidity. Other metal ions may be exchanged into the clay in order to tailor the level of catalytic Lewis acidity.

A preferred catalyst is a pillared clay, preferably an aluminium pillared clay, that has been treated with metal cations, for example, with aluminium nitrate.

Preferred metals for use in exchange and pillaring are selected from the group consisting of aluminium, zirconium, titanium and copper; and is most preferably aluminium.

Preferably, the furan-2,5-carboxylic acid dialkyl ester (preferably furan-2,5-carboxylic acid diethyl ester) is first pre-adsorbed onto the clay catalyst. This is advantageous because it was found to minimise sublimation of the furan-2,5-carboxylic acid dialkyl ester.

A preferred method of pre-adsorbing the furan-2,5-carboxylic acid dialkyl ester onto the clay comprises the steps of dissolving the furan-2,5-carboxylic acid dialkyl ester in a solvent (preferably ethanol), adding the clay catalyst, then removing the ethanol solvent using a vacuum and heating.

Conversion to PET

Preferably the process further comprises the step of converting the dialkyl terephthalate into a further product, preferably selected from the group consisting of terephthalate polyesters (most preferably polyethylene terephthalate), poly(butyleneterphalate-co-butyleneadipate) (PBAT), and terephthalate plasticizers (which are terephthalate diesters where the alkyl groups are longer carbon chains selected from straight and branched). Preferably, diethyl terephthalate is converted into polyethylene terephthalate.

Other ingredients may be added to the PET polymer. Those of ordinary skill in the art would readily be able to select the suitable ingredient(s) to add to the PET polymer to improve the desired properties, which may depend on the type of application intended. In a particular embodiment, the PET polymer may further comprise a supplemental component selected from at least one colouring agent, at least one fast re-heat additive, at least one gas barrier additive, at least one UV blocking additive, and a combination thereof.

The PET polymers may be used to form resins, which may be further processed into containers using methods including, but not limited to, injection moulding and stretch blow moulding.

Embodiments of the invention will now be illustrated by the following examples.

EXAMPLES

Example 1: Preparation of Catalysts CAT1-CAT5 for Use in a Process in Accordance with the Invention and Comparative Catalysts CATA and CATB The following catalysts were prepared:
CAT1-CAT5: in accordance with the invention
CATA and CATB: comparative examples
CAT1 was an Aluminium exchanged clay, prepared using Al nitrate and "Monmorillonite" clay obtained from Sigma Aldrich.
CAT2 was an Aluminium pillared clay, obtained from Sigma Aldrich.
CAT3 was the Aluminium pillared clay (CAT2), treated with aluminium nitrate.
CAT4 was the Aluminium pillared clay, pre-treated with furan-2,5-carboxylic acid diethyl ester.
CAT5 was CAT1 with pre-adsorbed reagent.
CATA was Zeolite Y (obtained from Sigma Aldrich).
CATB was CATA with pre-adsorbed reagent.

Process for Preparing Cation Exchanged Clays

Montmorillonite clay and Aluminium pillared clay were exchanged with metal ions as follows:

1.86 mmol of the desired metal nitrate (e.g. aluminium nitrate) was dissolved in 60 ml of distilled water. To this metal nitrate solution 1 g of montmorillonite clay or Al pillared clay was added and the suspension heated to 60° C. for 18 hours. The suspension was subsequently centrifuged and the liquor decanted off leaving the exchanged clay catalyst. The catalyst was washed several times with distilled water and centrifuged again before being dried in a vacuum oven at 80° C. for 5 hours.

Process for Pre-Adsorbing furan-2,5-carboxylic acid diethyl ester onto catalyst

Typically 1 g of furan-2,5-carboxylic acid diethyl ester was dissolved in 20 ml of ethyl acetate and then 1 g of catalyst (CAT1, CAT2, CAT3 or CAT4) added. The suspension was then placed on a rotary evaporator and rotated without vacuum or heat for 30 minutes. After 30 minutes of rotation both heat (50° C.) and vacuum (25 mbar) were applied to remove the ethyl acetate, whilst rotation was increased to maximum speed. Once all the solvent was removed the sample was placed under high vacuum (1 mbar) overnight. Finally, the collected solid was ground with a pestle and mortar to ensure homogeneity.

The level of pre-adsorption was varied from 50:50 to 60:40 by weight of FDEE:catalyst.

Pressurised reactions of furan-2,5-carboxylic acid diethyl ester with ethene were performed as follows:

Catalyst and furan-2,5-carboxylic acid diethyl ester were added to a high-pressure reactor, which was then purged with nitrogen. Ethene was then added to the reactor (40 bar fill pressure, 20° C.).

Amount of catalyst was varied between 0.15-0.5 g
Amount of ethene was varied between 80-100 ml.
Amount of furan-2,5-carboxylic acid diethyl ester was 0.5 g
Reaction temperature was varied between 150° C.-250° C.; and the
Reaction time was 24-48 hours.

After the allotted reaction time, the reactor was slowly vented. All solid and liquid material was washed from the reactor using ethyl acetate and the catalyst filtered from the resulting suspension. The ethyl acetate was removed in vacuo to typically yield a yellow oil.

The effect of reaction conditions, pre-adsorption of reagent and catalyst on the conversion, yield and selectivity of the process was determined. The results are given in the following examples.

Example 2: Conversion, Yield and Selectivity Using Catalyst CAT5 (Aluminium Exchanged Clay with Pre-Absorbed furan-2,5-carboxylic acid diethyl ester)

TABLE 1

Conversion, yield and selectivity using CAT 5 - a process in accordance with the invention

| Catalyst | Pre-ads loading | Temp ° C. | Pressure$_f$/Pressure$_r$ (bar) | Time (h) | Conversion/Yield/ Selectivity (%)*$^\infty$ |
|---|---|---|---|---|---|
| CAT 5 | 50:50 | 150 | 80/230 | 24 | 18/17/94 |
| | 50:50 | 150 | 80/150 | 48 | 48/36/75 |
| | 50:50 | 150 | 60/140 | 48 | 34/34/100 |
| | 50:50 | 200 | 60/130 | 24 | 56/37/66 |
| | 50:50 | 200 | 60/140 | 48 | 66/44/66 |

TABLE 1-continued

Conversion, yield and selectivity using CAT 5 - a process in accordance with the invention

| Catalyst | Pre-ads loading | Temp ° C. | Pressure$_f$/Pressure$_r$ (bar) | Time (h) | Conversion/Yield/ Selectivity (%)*$^\infty$ |
|---|---|---|---|---|---|
| | 60:40 | 200 | 60/160 | 48 | 96/61/63 |
| | 60:40 | 250 | 60/230 | 48 | 65/28/43 |

Pressure$_f$ = fill pressure;
Pressure$_r$ = reaction pressure

It will be seen that excellent yields are obtained with the CAT5 catalyst, in a process in accordance with the invention.

Example 3: Conversion, Yield and Selectivity Using Catalysts CATA (Aluminium-Y-Zeolite) and CATB (with Pre-Adsorbed Reagent)

TABLE 2

Conversion, yield and selectivity using CATA and CATB - a comparative process.

| Catalyst | Pre-ads loading | Temp ° C. | Pressure$_f$/Pressure$_r$ (bar) | Time (h) | Conversion/Yield/ Selectivity (%)*$^\infty$ |
|---|---|---|---|---|---|
| CATA | 0 | 200 | 60/130 | 24 | 0/0/0 |
| CATB | 50:50 | 200 | 60/130 | 24 | 0/0/0 |
| CATA | 0 | 250 | 60/140 | 24 | 6/6/100 |

Pressure$_f$ = fill pressure;
Pressure$_r$ = reaction pressure

It will be seen that the zeolite comparative produces very poor conversion and yield, even with pre-adsorption of the reagent.

Example 4: Conversion, Yield and Selectivity Using Catalyst CAT3 (Aluminium-Pillared Clay with Preadsorbed Reagent

TABLE 3

Conversion, yield and selectivity using CAT3 - process in accordance with the invention.

| Catalyst | Pre-ads loading | Temp ° C. | Pressure$_f$/Pressure$_r$ (bar) | Time (h) | Conversion/Yield/ Selectivity (%)*$^\infty$ |
|---|---|---|---|---|---|
| CAT3 | 50:50 | 150 | 60/120 | 48 | 0/0/0 |
| | 50:50 | 200 | 60/160 | 48 | 19/17/88 |
| | 50:50 | 200 | 70/160 | 48 | 8/5/63 |
| | 50:50 | 250 | 60/150 | 6 | 23/20/87 |
| | 50:50 | 250 | 60/230 | 48 | 68/50/74 |
| | 50:50 | 250 | 70/170 | 48 | 51/48/94 |
| | 60:40 | 200 | 60/160 | 48 | 18/17/97 |
| | 60:40 | 250 | 60/250 | 24 | 66/59/88 |
| | 60:40 | 250 | 60/250 | 48 | 81/51/63 |

Pressure$_f$ = fill pressure;
Pressure$_r$ = reaction pressure

It will be seen that excellent yields are obtained with the CAT3 catalyst, in a process in accordance with the invention. The CAT3 catalyst required a temperature of over 150° C. to function.

Example 5: Conversion, Yield and Selectivity During Re-Use of Catalyst CAT2 (Aluminium-Pillared Clay)

Catalyst CAT2 was reused in the reaction of furan-2,5-carboxylic acid diethyl ester with ethene, under batch conditions, in accordance with the invention.

TABLE 4

Conversion, yield and selectivity on reuse of CAT2 in a process in accordance with the invention.

| No. of use cycles | Conversion (%) | Yield (%) | Selectivity (%) |
|---|---|---|---|
| First use | 52 | 42 | 81 |
| Second use | 26 | 25 | 96 |
| Third use | 23 | 15 | 67 |

It will be seen that the catalyst performs well when re-used and displays excellent selectivity. Improved results would be expected under flow conditions.

The invention claimed is:

1. A process for preparing dialkyl terephthalate comprising:
    esterifying furan-2,5-dicarboxylate with an alcohol to form furan-2,5-carboxylic acid dialkyl ester; and
    reacting the furan-2,5-carboxylic acid dialkyl ester with ethylene under Diels Alder conditions, elevated temperature and pressure and in the presence of a catalyst such that dialkyl terephthalate is produced;
    wherein the Diels-Alder reaction is free from solvent; and
    wherein the catalyst comprises a clay comprising metal ions and having Lewis acidity.

2. The process as claimed in claim 1 further comprising converting the dialkyl terephthalate into a product selected from the group consisting of a) terephthalate polyesters, b) poly(butyleneterephthalate-co-butyleneadipate and c) terephthalate plasticizers, which are terephthalate diesters where the alkyl groups are longer carbon chains selected from straight and branched.

3. The process as claimed in claim 1, wherein the dialkyl terephthalate is diethyl terephthalate.

4. The process as claimed in claim 2, comprising converting the dialkyl terephthalate into polyalkylene terephthalate.

5. The process as claimed in claim 1, wherein the alcohol is a bioalcohol.

6. The process as claimed in claim 1, wherein the alcohol is selected from an aliphatic alcohol, a benzyl alcohol and a phenolic alcohol.

7. The process as claimed in claim 1, wherein the alcohol is selected from the group consisting of bio-methanol, bio-ethanol, bio-propanol, and mixtures thereof.

8. The process as claimed in claim 1, wherein an intermediate is formed during the Diels-Alder reaction, which is a bi-cyclic oxo-adduct.

9. The process as claimed in claim 1, wherein the clay is a smectite clay selected from the classes of the montmorillonites, hectorites, volchonskoites, nontronites, saponites, beidelites and sauconites.

10. The process as claimed in claim 1, wherein the catalyst is selected from cation-exchanged clays and pillared clays.

11. The process as claimed in claim 10, wherein the cation is selected from the group consisting of aluminium, zirconium, titanium and copper.

12. The process as claimed in claim 10, wherein the pillared clay is selected from the group consisting of aluminium pillared clay, zirconium pillared clay, titanium pillared clay and copper pillared clay.

13. The process as claimed in claim 1, wherein the furan-2,5-carboxylic acid dialkyl ester is pre-adsorbed onto the clay catalyst.

14. The process as claimed in claim 1, which is a batch process.

15. The process as claimed in claim 2, comprising converting the dialkyl terephthalate into polyethylene terephthalate.

16. The process as claimed in claim 7, wherein the alcohol is bio-ethanol.

17. The process as claimed in claim 9, wherein the clay is a montmorillonite clay.

18. The process as claimed in claim 10, wherein the catalyst is pillared clays.

19. The process as claimed in claim 11, wherein the cation is aluminium.

20. The process as claimed in claim 12, wherein the pillared clay is aluminium pillared clay.

21. The process as claimed in claim 13, wherein pre-adsorbing the furan-2,5-carboxylic acid dialkyl ester onto the clay catalyst comprises:
    dissolving the furan-2,5-carboxylic acid dialkyl ester in a solvent;
    adding the clay catalyst; and
    removing the solvent using a vacuum and heating.

22. The process as claimed in claim 21, wherein the solvent is selected from ethanol, ethyl acetate or a mixture thereof.

* * * * *